United States Patent
Hayden et al.

(10) Patent No.: US 11,079,718 B2
(45) Date of Patent: Aug. 3, 2021

(54) SPECIFIC MALARIA DETECTION WITH DIGITAL HOLOGRAPHIC MICROSCOPY

(71) Applicant: Siemens Healthcare GmbH, Erlangen (DE)

(72) Inventors: Oliver Hayden, Moosburg (DE); Lukas Richter, Hirschaid (DE); Matthias Ugele, Neumarkt (DE); Gaby Marquardt, Hausen (DE); Manfred Stanzel, Berching (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/651,996

(22) PCT Filed: Sep. 25, 2018

(86) PCT No.: PCT/EP2018/075966
§ 371 (c)(1),
(2) Date: Mar. 27, 2020

(87) PCT Pub. No.: WO2019/063548
PCT Pub. Date: Apr. 4, 2019

(65) Prior Publication Data
US 2020/0264557 A1 Aug. 20, 2020

(30) Foreign Application Priority Data
Sep. 29, 2017 (EP) .................... 17193959

(51) Int. Cl.
*G03H 1/04* (2006.01)
*G01N 33/49* (2006.01)
(Continued)

(52) U.S. Cl.
CPC ....... *G03H 1/0443* (2013.01); *G01N 33/4915* (2013.01); *G01N 15/14* (2013.01);
(Continued)

(58) Field of Classification Search
CPC .......... G03H 1/0443; G03H 2001/005; G03H 2001/0471; G01N 33/4915; G01N 15/14;
(Continued)

(56) References Cited

U.S. PATENT DOCUMENTS

| | | | |
|---|---|---|---|
| 6,524,858 B1 * | 2/2003 | Zelmanovic | G01N 15/14 422/73 |
| 7,903,241 B2 * | 3/2011 | Wardlaw | G01N 15/05 356/39 |

(Continued)

FOREIGN PATENT DOCUMENTS

| | | |
|---|---|---|
| CN | 105717312 A | 6/2016 |
| DE | 102014205535 | 10/2015 |

(Continued)

OTHER PUBLICATIONS

Gascoyne, Peter et al.: "Microsample preparation by dielectrophoresis isolation of malaria"; Lab Chip; pp. 70-75; Royal Society of Chemistry; 2002.
(Continued)

*Primary Examiner* — Michael P LaPage
(74) *Attorney, Agent, or Firm* — Dugan & Dugan, PC

(57) ABSTRACT

The present invention relates to a method of detecting a possible infection of malaria in a patient using a digital optical microscope.

10 Claims, 2 Drawing Sheets

(51) Int. Cl.
  *G01N 15/14* (2006.01)
  *G03H 1/00* (2006.01)
(52) U.S. Cl.
  CPC ............... *G03H 2001/005* (2013.01); *G03H 2001/0471* (2013.01)
(58) Field of Classification Search
  CPC ............. G01N 15/1434; G01N 15/147; G01N 15/1484; G01N 2015/0073; G01N 2015/1454; G01N 2015/1006
  See application file for complete search history.

(56) References Cited

U.S. PATENT DOCUMENTS

| | | | |
|---|---|---|---|
| 2005/0134833 A1* | 6/2005 | Kramer | G01N 15/1459 356/39 |
| 2007/0190525 A1* | 8/2007 | Gu | G01N 15/1459 435/5 |
| 2014/0333929 A1 | 11/2014 | Sung et al. | |
| 2017/0357211 A1* | 12/2017 | Moon | G03H 1/0404 |

FOREIGN PATENT DOCUMENTS

| | | |
|---|---|---|
| WO | WO2012142664 | 10/2012 |
| WO | WO 2015195642 | 12/2015 |
| WO | WO 2017157555 | 9/2017 |

OTHER PUBLICATIONS

Rappaz, Benjamin et al.: "Comparative Study of Human Erythrocytes by Digital Holographic Microscopy, Confocal Microscopy, and Impedance Volume Analyzer", Cytometry Part A; International Society for Advancement of Cytometry; Jul. 9, 2008; pp. 895-903 DOI: 10.1002/cyto.a.20605; 2008.
Anand, A. et al.: "Automatic Identification of Malaria-Infected RBC With Digital Holographic Microscopy Using Correlation Algorithms"; IEEE Photonics Journal; vol. 4, No. 5; Oct. 2012; pp. 1456-1464; DOI: 10.1109/JPHOT.2012.2210199; 2012.
Kim, Young Ran: "Isovolumetric Sphering of Erythrocytes for More Accurate and Precise Cell Volume Measurement by Flow Cytometry"; vol. 3; No. 6; 1983; USA; pp. 419-427; Cytometry; Society for Analytical Cytology; DOI: 0196-4763/83/0306-041900.00/0; 1983.
Memmolo, Pasquale et al.: "3D Morphometry of Red Blood CeUs by Digital Holography"; Cytometry Part A; International Society for Advancement of Cytnmetry; Sep. 19, 2014; pp. 1030-1036 DOI: 10.1002/cyto.a.22570; 2014.
He, Xuefei et al: "Mapping the progression of malaria infected erythrocytes with holographic microscopy", 2015 11th Conference on Lasers and Electro-Optics Pacific Rim (CLEO-PR), IEEE, vol. 3, pp. 1-2, XP032841305, DOI: 10.1109/CLEOPR.2015.7376546; the whole document; 2015.
Park, Han Sang et al: "Automated Detection of P. falciparum Using Machine Learning Algorithms with Quantitative Phase Images of Unstained Cells", PLOS ONE, vol. 11, No. 9, pp. e0163045, XP055446890, DOI:10.1371/journal.pone.0163045, the whole document; 2016.
Park, Yongkeun et al.:"Refractive index maps and membrane dynamics of human red blood cells parasitized by Plasmodium falciparum"; in: PNAS; vol. 105; No. 37; pp. 13730-13735; Sep. 2008.
Patel, Nimit R et al: "Identification of malaria infected red blood samples by digital holographic quantitative phase microscope", Progress in Biomedical Optics and Imaging, SPIE—International Society for Optical Engineering, Bellingham, WA, US, vol. 9536, pp. 95360E-95360E, XP060056528, ISSN: 1605-7422, DOI: 10.1117/12.2183746 ISBN: 978-1-5106-0027-0; pp. 1-3, Fig. 1; 2015.
Seo, Kyung Won et al.:"Vertical focusing and cell ordering in a microchannel via viscoelasticity: Applications for cell monitoring using a digital holographic microscopy"; in: Applied Physics Letters; vol. 104; 213702; 2014; doi:http://dx.doi.org/10.1063/1.4880615.
Silamut, K. et al.: "Relation of the stage of parasite development in the peripheral blood to prognosis in severe falciparum malaria."; in: Transactions of the Royal Society of Tropical Medicine Hygiene; vol. 87; No. 4; 1993.
Yang, Dahou et al.: "A portable image-based cytometer for rapid malaria detection and quantification", PLOS ONE, vol. 12, No. 6, Jun. 8, 2017 (Jun. 8, 2017), pp. e0179161, XP055446896, DOI:10.1371/journal.pone.0179161, pp. 1-2, Fig. 1; 2017.
White N. J. et al.: "The effects of multiplication and synchronicity on the vascular distribution of parasites in falciparum malaria"; in: Transactions of the Royal Society of Tropical Medicine and Hygiene; vol. 86; No. 6; pp. 590-597; 1992.
Jorgensen, Michael B., "Automated Point-of-Care Image Processing Methodology for the Diagnosis of Malaria" (2013).Master's Theses. 387. http://digitalcommons.uconn.edu/gs_theses/387.
Jagannadh , Veerendra Kalyan et al.: "A semi-automated, field-portable microscopy platform for clinical diagnostic applications"; AIP Advances 5.
Lee, Seung Ah et al.:; "Color Capable Sub-Pixel Resolving Optofluidic Microscope and Its Application to Blood Cell Imaging for Malaria Diagnosis"; PLoS ONE; Oct. 2011; vol. 6; Issue 10.
Wu, Tenghu et al.;: "Simulation of malaria-infected red blood cells in microfluidic channels: Passage and Blockage"; Biomicrofluidics 7, 044115 (2013).
International Search Report and Written Opinion of International Application No. PCT/EP2018/075966 dated Nov. 6, 2018.
Search Report of EP Application No. 17193959.8 dated Feb. 9, 2018.

\* cited by examiner

SPECIFIC MALARIA DETECTION WITH DIGITAL HOLOGRAPHIC MICROSCOPY

CROSS REFERENCE TO RELATED APPLICATIONS

This is a 371 of PCT/EP2018/075966, filed Sep. 25, 2018, which claims priority to European Patent Application No. EP 17193959.8, filed Sep. 29, 2017, both of which are hereby incorporated by reference herein in their entireties for all purposes.

FIELD

The present invention relates to a method of detecting a possible infection of malaria in a patient using a digital optical microscope (DHM).

BACKGROUND

Malaria detection suffers from general measurement problems, as it (1) requires a fast detection (molecular-diagnostic tests are not sufficiently fast enough and typically take 3 h), (2) requires good sensitivity (parasitemia <0.1%; golden standard thick film diagnostic), (3) has to be specific (at present only achievable quantitatively by thin film microscopy) and (4) especially should only require low cost (primary qualitative rapid tests based on lateral flow assays; 1 USD/test). Curiously, the malaria rapid tests especially in African countries lead to a decrease of microscopy use, which results in a loss of diagnostic information. On the other hand, a malaria infection can usually only be determined indirectly with a hematology analyzer using apparatus-specific deviation, of white blood cells (WBC) or platelets, from normal blood.

Of clinical relevance until today is manual microscopy of thin (specificity) and thick (sensitivity) films for initial diagnostics and differential diagnostics in therapy. In resource weak regions, preferably rapid tests are used for the initial diagnostics. Generally, a parasitemia is detected by lysis and staining of a thick film, and the specificity by microscopy of the dried and stained erythrocytes.

However, the above methods suffer from the above problems, and cannot fulfil all the above criteria.

Therefore, there remains a need for an improved method of detecting a possible infection of malaria in a patient which is reliable, fast, and relatively cheap and can achieve quantitative results.

SUMMARY OF THE INVENTION

The inventors developed a specific sequence of method steps for determining a work flow for malaria detection using digital holographic microscopy (DHM), particularly with a simple microfluidic flow scheme, which allows measurement of all the above aspects (1) to (4) with a performance of clinical relevance, particularly requiring almost no sample preparation. The measurement can be integrated in imaging flow cytometry, which will play an important role for hematologic routine diagnostic in the future.

The present invention relates to a method of detecting a possible infection of malaria in a patient, comprising:
providing a digital optical microscope (DHM),
obtaining or providing a sample comprising at least one red blood cell suspected of being affected by malaria from the patient,
mixing the sample comprising the at least one red blood cell with a buffer solution to form the at least one red blood cell into a sphere shape to form a sphere-shaped red blood cell, and introducing the buffer solution comprising the at least one sphere-shaped red blood cell into a microfluidic device, wherein at least one part of a channel of the microfluidic device is comprised in a focal area of the DHM, and/or
introducing the sample comprising the at least one red blood cell into a microfluidic device, and mixing the sample comprising the at least one red blood cell with a buffer solution to form the at least one red blood cell into a sphere shape to form a sphere-shaped red blood cell, wherein at least one part of a channel of the microfluidic device is comprised in a focal area of the DHM,
guiding the at least one sphere-shaped red blood cell into the focal area of the DHM,
detecting the at least one sphere-shaped red blood cell with the DHM, and
determining whether the at least one red blood cell is affected by malaria to determine whether the patient is infected by malaria.

Further aspects and embodiments of the invention are disclosed in the dependent claims and can be taken from the following description, figures and examples, without being limited thereto.

BRIEF DESCRIPTION OF THE DRAWINGS

The enclosed drawings should illustrate embodiments of the present invention and convey a further understanding thereof. In connection with the description, they serve as explanation of concepts and principles of the invention. Other embodiments and many of the stated advantages can be derived in relation to the drawings. The elements of the drawings are not necessarily to scale towards each other. Identical, functionally equivalent and acting equal features and components are denoted in the figures of the drawings with the same reference numbers, unless noted otherwise.

DETAILED DESCRIPTION OF THE INVENTION

Definitions

Figure 1:
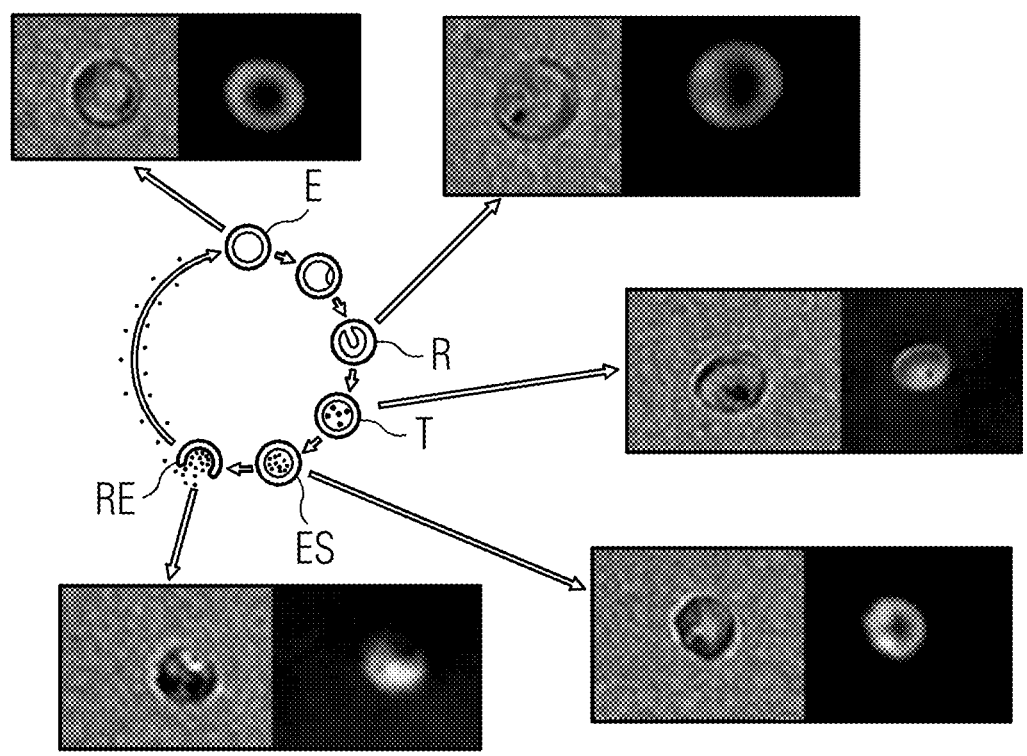
FIG. 1 shows schematically how a differentiation of different malaria species with DHM is possible.

Unless defined otherwise, technical and scientific terms used herein have the same meaning as commonly understood by one of ordinary skill in the art to which this invention belongs.

In the context of the present invention a "sample" is a sample to be analyzed for a possible infection of malaria which comprises at least one red blood cell/erythrocyte, e.g., 1, 2, 3, 4, 5, 6, 7, 10, 100, 1000, 10000, 100000 or more red blood cells. The form of the red blood cell as well as the state of the sample therein is not particularly restricted, and it can be, e.g., a sample that is obtained or given at a temperature in any location of the world, e.g., also ranging from −20° C. and below to 50° C. or more, e.g., from −10° C. to 45° C., or from 0° C. to 40° C., or from 10° C. to 35° C., but can be also at a room temperature of 20-25° C.

The sample is not particularly restricted and can be of natural or synthetic origin and can, e.g., comprise samples from simple or complex matrices, as long as it comprises at least one red blood cell, e.g., can be from a subject, e.g., a vertebrate, e.g., a human or animal. It can also be a sample that has been previously enriched, extracted, filtered, or treated any other way in order to enrich red blood cells or in order to separate the red blood cells from an original sample. The sample can also be water-free or water-poor. The sample can even be a sample essentially containing only red blood cells, e.g., after they were centrifuged of an original sample, or a sample only containing blood cells, etc. According to certain embodiments, the at least one red blood cell is isolated from an original sample of the patient, preferably a blood sample, providing a sample preferably comprising essentially the at least one red blood cell, or preferably comprising essentially a multitude of red blood cells.

According to certain embodiments, the sample is an aqueous sample, i.e., a sample containing water. For example, the sample can be a body fluid of a subject. Body fluids are thereby liquids originating from inside the bodies of subjects, particularly living subjects. They include fluids that can be excreted or secreted from the body and/or that circulate in the body, and body water. They can be in the state of a liquid, emulsion, or suspension. Examples of body fluids within the invention are particularly blood and samples derived thereof if they at least comprise at least one red blood cell. According to certain embodiments, the sample is a patient sample (clinical isolate). An exemplified sample is whole blood of a patient.

According to certain embodiments, the subject in the present method of extracting a substance from a sample, enriching a substance in a sample, and/or detecting a substance in a sample can be a vertebrate, preferably a human or animal, more preferably a mammal and most preferred a human, respectively human patient.

A vertebrate within the present invention refers to animals having a vertebrate, which includes mammals—including humans, birds, reptiles, amphibians and fishes. The present invention thus is not only suitable for humans and the human medical field, but also for veterinary medicine. This means that also a possible infection of an animal with malaria can be detected, e.g., of domesticized animals after travelling on board planes, ships, etc., e.g., from regions prone to malaria outbreaks.

The focal area of the DHM is the area around the focal point of the DHM wherein at least 50% of the light irradiated by a detection beam of the DHM, preferably at least 80%, further preferably at least 90%, e.g., at least 95%, 98%, 99%, or even up to 100% can be detected.

In the present description, all numerical values relating to amounts are understood to be given in wt. %, unless given otherwise or clear from context that something else is intended.

Before the invention is described in exemplary detail, it is to be understood that this invention is not limited to the particular component parts of the process steps of the methods described herein as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. For example, the term "a" as used herein can be understood as one single entity or in the meaning of "one or more" entities. It is also to be understood that plural forms include singular and/or plural referents unless the context clearly dictates otherwise. It is moreover to be understood that, in case parameter ranges are given which are delimited by numeric values, the ranges are deemed to include these limitation values.

The present invention relates to a method of detecting a possible infection of malaria in a patient, comprising:
  providing a digital optical microscope (DHM),
  obtaining or providing a sample comprising at least one red blood cell suspected of being affected by malaria from the patient,
  mixing the sample comprising the at least one red blood cell with a buffer solution to form the at least one red blood cell into a sphere shape to form a sphere-shaped red blood cell, and introducing the buffer solution comprising the at least one sphere-shaped red blood cell into a microfluidic device, wherein at least one part of a channel of the microfluidic device is comprised in a focal area of the DHM, and/or
  introducing the sample comprising the at least one red blood cell into a microfluidic device, and mixing the sample comprising the at least one red blood cell with a buffer solution to form the at least one red blood cell into a sphere shape to form a sphere-shaped red blood cell, wherein at least one part of a channel of the microfluidic device is comprised in a focal area of the DHM,
  guiding the at least one sphere-shaped red blood cell into the focal area of the DHM,
  detecting the at least one sphere-shaped red blood cell with the DHM, and
  determining whether the at least one red blood cell is affected by malaria to determine whether the patient is infected by malaria.

In the present method, the providing of the DHM and the digital holographic microscope itself are not particularly restricted, and can be in any form. Using a coherent light source and at least a beam splitter, a holographic image of the sample can be constructed using the digital holographic microscope, and the setup thereof is not particularly restricted. The digital holographic microscope works using a reference beam and a detection beam which can be suitably set in different beam setups, e.g., on axis, off-axis, perpendicular, etc. As necessary, objective lenses, further beam splitters, condensers, etc., can be present.

Digital holographic microscopy using the DHM can be, e.g., performed in transmission or optional reflection mode and can be performed referentially with a common beam setup. The contrast is the result of scatter effects of subtle refractive index changes between the medium and cells as well as in between subcellular components. The quantitative and integral phase information of the subcellular components is related to Mie scatter.

Preferably measurement is carried out off-axis so that a simpler and more robust interference setup can be achieved and the measurement distance is short, thus minimizing noise. Thus, according to certain embodiments, a reference beam and a detection beam of the digital holographic microscopic device are off axis. Also, preferably measurement is done in transmission mode.

The depth of field is preferably 5.7 µm or less, more preferably 4.7 µm or less, e.g., 3 or 2 µm or less, particularly preferably 1.5 µm or less. With a reduced depth of field, a good lateral resolution can be achieved as well, facilitating cell discrimination. At a low depth of field, further cell compartments in the cells like granulae in white blood cells can be easily observed and discriminated, allowing for improved discrimination of the cells. Also, further information like phase information can be better obtained with reduced depth of field.

The use of a microfluidic device/system can achieve a focusing of red blood cells to be detected so that they can even be easily guided through a reduced depth of field and thus preferably even be quantified, even in flowing conditions.

Further, the applied microfluidic device can achieve a scalable recording of different cell numbers, e.g., $1*10^3$ to $>1*10^6$ cells, e.g., up to $1*10^7$. According to certain embodiments, $1*10^4$ to $1*10^6$ red blood cells are detected. This way, also very small parasitemias in the ppb range can be detected. The analysis thus—in contrast to previous detection methods like, e.g., rapid tests or PCR—can be adapted individually to an intended diagnosis or treatment without additional effort. Particularly, also a fluctuating number of existing circulating stages at different times after the infection due to synchronization can be resolved (see NJ White et al., 1992, "The effects of multiplication and synchrony on the vascular distribution of parasites in falciparum malaria", Trans R Soc Trop Med Hyg, 86(6), pp. 590.7).

According to certain embodiments, the detection of the at least one sphere-shaped red blood cell, e.g., more than one red blood cell, is carried out while flowing the buffer solution comprising the at least one red blood cell through the microfluidic device. The flow is not particularly limited as long as the at least one red blood cells is flown past the digital holographic microscope/microscopic device at a speed that allows for taking an image thereof that is not blurred, which is, e.g., depending on the illumination time, etc., for obtaining an image with enough contrast. Also a flow that is too slow should be preferably avoided to achieve a sufficient throughput. The flow can be set suitably depending on parameters of the digital holographic microscope as well as the microfluidic device, e.g., the dimensions of the microfluidic channel(s), surface conditions thereof, etc.

According to certain embodiments, the flow in the microfluidic device is at least laminar in a region wherein the image of the at least one cell is obtained. With a laminar flow, the cells can be set to a preferable orientation so that they can be easily detected. A laminar flow can be suitably set depending on, e.g., dimensions within the microfluidic device.

According to certain embodiments, the microfluidic device comprises a microchannel in the region wherein the at least one red blood cell is detected, preferably in which a laminar flow is produced by at least one sheath flow. The size and shape of the microchannel is therein not particularly restricted. According to certain embodiments, the microchannel is rectangular or square in a cross-section, particularly at least in a region wherein the at least one red blood cell is detected by the DHM.

With a microchannel, the flow can be easily set and determined, so that quantification can be simplified. Also, a sheath flow can be easily implemented in a microchannel. Preferably, a sheath flow is implemented for at least two opposing sites in the microchannel to achieve a focusing of red blood cells to be detected. Further preferably, a sheath flow is implemented from two, particularly four—preferably perpendicular—directions in the microchannel, particularly in a rectangular or square microchannel (e.g., at the top, bottom, left, and right), to achieve a suitable focusing and cell orientation. The sheath flows can be implemented by, e.g., flowing of further microfluidic flows from different inlets compared to a main channel.

According to certain embodiments, the field of view of the digital holographic microscopic device is at most 1.0 times the width of the microchannel in a region wherein the at least one red blood cell is detected, e.g., an image of the at least one red blood cell is obtained.

According to certain embodiments, the microchannel comprises at least one surface, preferably at least two surfaces perpendicular to a wavefront of a reference and/or detection beam of the digital holographic microscope.

According to certain embodiments, the surfaces of the microchannel perpendicular to a wavefront of a reference and/or detection beam of the digital holographic microscopic device are essentially planar. This can avoid disturbances and/or reflections of the wave fronts of the reference beam and/or the detection beam, facilitating signal analysis and image reconstruction, as well as obtaining of further information like phase information essentially without adjustments in calculations due to such disturbances, reflections, etc.

Furthermore, the obtaining or providing of a sample comprising at least one red blood cell suspected of being affected by malaria from the patient is not particularly restricted. It can be obtained or provided, e.g., in vitro according to certain embodiments. As stated above, it is not excluded that the sample is a sample that was treated prior to this obtaining of providing of the sample.

In the present invention, the mixing of the sample comprising the at least one red blood cell and a buffer solution can be carried out outside the microfluidic device and/or inside the microfluidic device. The mixing thereby is not particularly restricted, and can be done outside the microfluidic device, e.g., by a shaker, a stirrer, etc., or can be done inside the microfluidic device by mixing structures, etc.

For the mixing, the buffer solution is not particularly restricted as long as it allows producing sphere-shaped red blood cells. It can be a buffer solution usually applied for analysis of red blood cells (RBC) in, e.g., hematology analyzers. For example, the erythrocytes in a sample can be spheroidized with a standard buffer solution comprising, e.g., from about 0.01 to about 0.5 Vol. %, e.g., about 0.1 Vol. % glutaraldehyde and/or another fixing agent, and about 0.02 to 0.05 mmol/L SDS (sodium dodecyl sulfate) and/or another surfactant, apart from suitable buffer substances and optionally chelating agents, both of which are not restricted. For the buffer solution, the solvent is not particularly restricted, and can, e.g., comprise or be water.

An exemplary aqueous buffer solution is as follows (amounts given with regard to the buffer solution):
  SDS (sodium dodecyl sulfate), 0.035 mmol/L, which affects the cell membrane
  buffer (pH 7.4), e.g. based on hydrogenphosphate/dihydrogenphosphate
  sodium chloride (109.3 mmol/L)
  glutaraldehyde (0.11 Vol. %)
  $Na_2EDTA$ (4.03 mmol/L)
  $Na_4EDTA$ (3.36 mmol/L)

With the buffer solution, the sample comprising the red blood cells can be diluted so that the red blood cells can be observed more easily by the DHM. A dilution of the red blood cells in the buffer solution—including possibly remainders of the sample—can be, e.g., in the range from 1:10 to 1:2000, preferably 1:20 to 1:2000, further preferably 1:25 to 1:700, e.g., 1:28 to 1:600, e.g., 1:29 to 1:200, e.g., 1:30 to 1:70, e.g., 1:30 to 1:50.

The introducing of the buffer solution comprising the RBC or the sample comprising the RBC as well as the buffer solution into the microfluidic device is not particularly restricted and can be done, e.g., via pumps and tubes, capillaries, syringes, or any other suitable introduction means for microfluidic devices.

The guiding of the at least one sphere-shaped red blood cell into the focal area of the DHM is also not particularly restricted, and can be done, e.g., as stated above by setting a suitable flow in the microfluidic device. In this regard, it is noted that also the objective lens can be guided with the focal area to the microfluidic flow alternatively or in addition, so that this is also not excluded.

Also, the detecting of the at least one sphere-shaped red blood cell with the DHM is not particularly restricted, as stated above.

Determining whether the at least one red blood cell is affected by malaria to determine whether the patient is infected by malaria can be carried out using different criteria as, e.g., also described below with regard to certain embodiments of the invention. For determining whether the at least one red blood cell is affected by malaria, the presence of cellular stages specific to malaria infection and/or parasitemia can be considered, for example, to determine in a first stage whether a malaria infection may be present.

According to certain embodiments, the detecting of the at least one sphere-shaped red blood cell with the DHM involves a reconstruction of the phase and amplitude image obtained by the DHM. This way, different further specific parameters particular to a malaria infection can furthermore be determined, as will be described below in more detail, apart from the cell shape which allows detecting the presence of malaria-specific cell stages, e.g., a ring stage or other stages also described in more detail below.

For an improved malaria diagnostic, an unambiguous differentiation between *malaria tertiana, malaria tropica*, and *malaria quartana* is advantageous. Thus, according to certain embodiments, *malaria tertiana, malaria tropica*, and *malaria quartana* are differentiated using the DHM measurement. Further, according to certain embodiments, the percentage of infected cells (parasitemia) is determined in the present method.

For differentiating the different malaria species, the following criteria can be applied:

1. Using the phase image of the DHM, the diameter of the spheroidized, infected erythrocytes, and thus their volume (volume of a sphere: $V=4/3*\pi*r^3$) can be determined. Using the determined volume, a first classification can be carried out: *M. tertiana* parasites (*P. vivax* or *ovale*) only infect reticulocytes and young erythrocytes with a size of 8 to 10 μm (in biconcave form). *M. tropica* parasites (*P. falciparum*) only infect normocytes with a size of 7 to 8 μm (in biconcave form). *M. quartana* parasites (*P. malariae*) infect only microcytes with a size of <7 μm (in biconcave form).

Thus, according to certain embodiments, the cell volume and/or cell diameter of the at least one sphere-shaped red blood cell is determined with the DHM to identify a development stage and species of the malaria parasite. According to certain embodiments, at least ⅔ of the volume of the at least one sphere-shaped red blood cell is detected with the DHM. The DHM measurement is particularly sensitive when >⅔ of the volume of a spheroidized RBC and/or reticulocyte is within the focal area of the objective lens. Typically, the diameter of a spheroidized RBC and a reticulocyte is >4 μm. It is to be noted that the present method of malaria diagnostics is independent of the viscoelastic properties of the cells, the hemoglobin concentration in the cells, and the orientation of the RBC in the sample, e.g., a suspension. Particularly, this last aspect enables a simple high throughput analysis, as is applied in a similar fashion in the hematological examination of RBC using flow cytometry.

However, an unambiguous differentiation only based on the size of the infected erythrocytes can lead to a wrong diagnosis, though, as the transition between reticulocytes, normocytes, and microcytes are fluent. In order to rule out a false diagnosis, further differentiation features can be used from the DHM result.

2. The presence of different malaria stages in peripheral blood also enables a differentiation of different malaria species. For *M. tertiana* and *M. quartana*, all stages of parasite development are present in circulating as well as in sequestered state in peripheral blood. A sharp synchronization only takes place when the illness becomes self-limiting. For *M. tropica*, ring stages and possibly trophozoite stages can be seen in circulation. In addition, multiple infestations with ring stages are also typical. With extremely high parasitemia also (rarely) sequestered stages can be found. In order to avoid a false diagnosis, a third differentiation criteria can be used.

Therefore, according to certain embodiments, a multitude of red blood cells is detected using the DHM, wherein different stages of the malaria species are determined for the multitude of red blood cells.

FIG. 1 shows that a full malaria life cycle is detectable with DHM label-free, including the ring-stage, which is the earliest detectable growth stage of a plasmodium infection. With the present method, specific malaria information can be provided at clinically relevant growth stages.

FIG. 1 shows a comparison of the different malaria stages with images obtained from a regular optical microscope (left; incident light micropcopy at magnification 40×; NA=0.55), and from a DHM (right; transmitted light; magnification 40×; NA=0.55). It shows the differences in cells observed in the erythrocyte (E), ring (R), trophozoite (T), erytrhocytic schizont (ES), and ruptured erythrocyte (RE) stage. As is clear thereof, DHM allows a differentiation of the different cell stages as well as an optical microscope.

3. Parasitemia is an additional feature for the differentiation of the different malaria types. For *M. tertiana*, parasitemia never increases beyond 2% as the infection is limited to reticulocytes—which typically account for at most 2% of the erythrocytes. For *M. quartana*, parasitemia also never increases beyond 2% as only small erythrocytes are infested. In contrast, significantly higher parasitemia—in extreme cases considerably higher than 10% —can occur for *M. tropica*, which thus represents an important feature for differentiation.

Thus, according to certain embodiments, the parasitemia of the multitude of red blood cells is determined, involving determining the ratio of the number of infected cells to the number of total cells. Parasitemia can be determined using the number of infected cells relative to the total number of detected cells.

Figure 3:
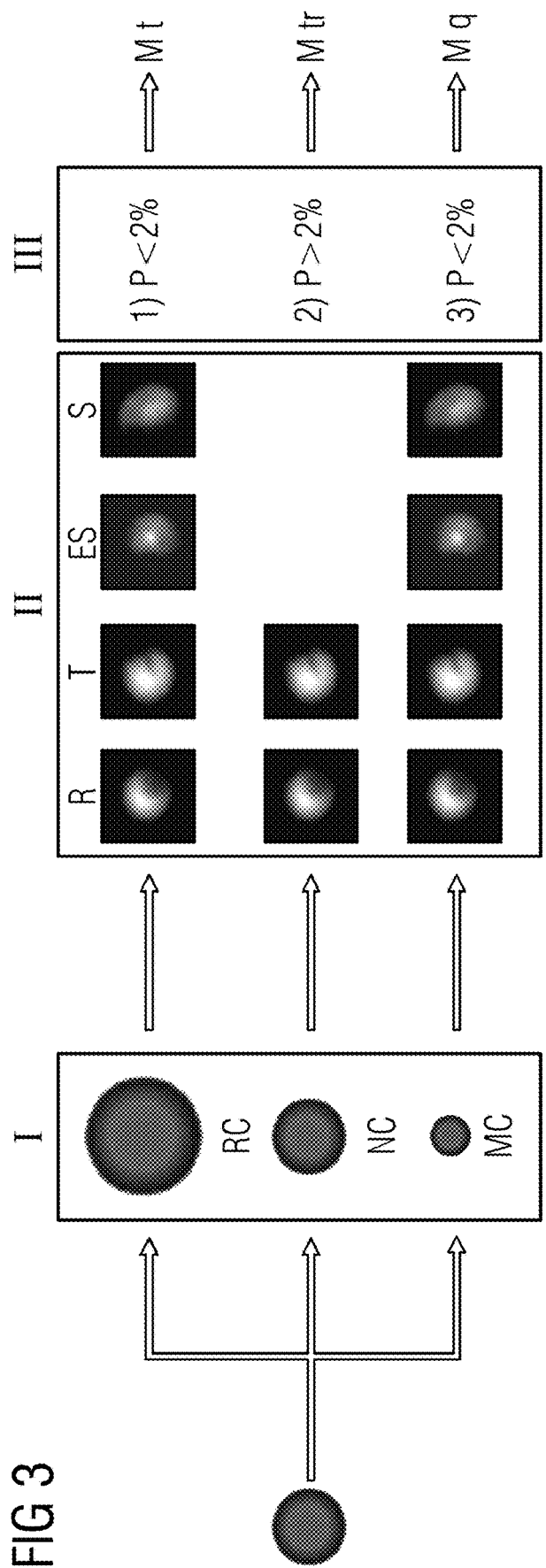
In FIG. 3 a schematic view of species differentiation is presented.

All three differentiation criteria can be applied in arbitrary sequence, however, a combination of all three criteria is of advantage for an unambiguous diagnosis. FIG. 3, which will be described in more detail later shows how a differentiation of different malaria species with DHM is possible.

According to certain embodiments, determination of the malaria type can be done with the help of a machine learning program which is not particularly restricted, wherein, e.g., several images of several reference cell types infected with different malaria species can be used to train the program.

Particularly to perform image analysis for malaria differentiation, machine learning based techniques can be used, which are not particularly restricted. In such techniques, the analysis is generally performed in two main phases: training phase and testing phase. These can be carried out as usual in image analysis of, e.g., DHM measurements.

The above embodiments can be combined arbitrarily, if appropriate. Further possible embodiments and implementations of the invention comprise also combinations of features not explicitly mentioned in the foregoing or in the following with regard to the Examples of the invention. Particularly, a person skilled in the art will also add individual aspects as improvements or additions to the respective basic form of the invention.

EXAMPLES

The present invention will now be described in detail with reference to several examples thereof. However, these examples are illustrative and do not limit the scope of the invention.

Example 1

In a first example, erythrocytes infected with *M. tertiana* (*P. ovale* and *P. vivax*), *M. tropica* (*P. falciparum*), and *M. quartana* (*P. malariae*) were first spheroidized separately with an aqueous standard buffer solution which is as follows:
  SDS (sodium dodecyl sulfate), 0.035 mmol/L, which affects the cell membrane
  buffer (pH 7.4), e.g. based on hydrogenphosphate/dihydrogenphosphate
  sodium chloride (109.3 mmol/L)
  glutaraldehyde (0.11 Vol. %)
  $Na_2EDTA$ (4.03 mmol/L)
  $Na_4EDTA$ (3.36 mmol/L)

Figure 2:
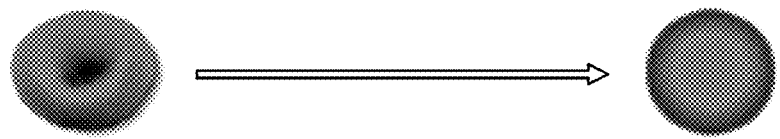
In FIG. 2 the spheroidization of a red blood cell is depicted schematically.

Images of the non-spheroidized RBC and the spheroidized RBC were taken for comparison and are shown in FIG. 2 (incident light microcopy at magnification 40×; NA=0.55), with the spheroidized RBC shown on the right.

With the separately infected RBCs, the differentiation between the different malaria species could then be carried out using DHM detection (transmitted light; magnification 40×; NA=0.55).

The dilution of the RBC in the buffer solution was adjusted to be about 1:600 for obtaining clear pictures of the spheroidized RBC in the example, although final dilution factors for high throughput in an analysis environment on site are aimed to be 1:20 to 1:200, e.g., 1:30 to 1:50.

As a microfluidic device, a simple rectangular microchannel (width 500 μm, height 50 μm) with one inlet and outlet is taken, where a part of the microchannel was positioned in the focal area of the DHM.

In the microchannel, the spheroidized RBCs were guided to the focal area of the objective lens (magnification 40×; NA=0.55) of the DHM by microfluidic guidance and a holographic image was recorded.

After an image reconstruction of the holographic image, the different stages of a malaria infection could be differentiated from the phase and amplitude image and the intracellular contrast. This surprising result was not expected as it was not known before that malaria diagnostics can be carried out on spheroidized cells using imaging methods alone.

Furthermore the DHM-based malaria diagnostics allowed identification of the development stage and the pathogen species using the high contrast and the volume determination of the erythrocytes, particularly with the aid of a machine algorithm, as the different malaria pathogens show a specific infection pattern of erythrocytes, as described above and shown in more detail below.

In this regard, it is noted that an identification of the development stage of the parasite species is additionally also possible with an evaluation of physical parameters alone instead of using a machine algorithm.

A detailed description of the differentiation of different malaria species by physical parameters is given in the following, particularly also with regard to FIG. 3, given for better understanding. FIG. 3 therein shows a schematic view of species differentiation.

As shown under I, the DHM measurement allowed a differentiation between reticulocytes (RC) with a diameter of between 8-10 μm, normocytes (NC) with a diameter of between 7-8 μm, and microcytes (MC) with a diameter of less than 7 μm.

Further, as shown in II, for the three different RBCs different malaria stages could be observed, with a ring stage (R) and a trophozoite stage (T) observed for all three (RC, NC and MC), whereas a schizont stage (ES) and a segmenter stage (S) was only observed for RC and MC.

In addition, by quantification of parasitemia P, as shown under criteria III, further differences were observed, with RC and MC showing parasitemia of <2%, and NC showing parasitemia >2% and multiple infections.

Accordingly, a predominant infection of RBC with all four stages and P<2% could be attributed to *M. tertiana*, a predominant infection of NC with only stages R and T and P>2% could be attributed to *M. tropica*, and the extremely rare infection of MC with all four stages and P<2% could be attributed to *M. quartana*. For a reference measurement, a quantification of infected cells was carried out by counting cell numbers under a microscope.

Example 2

In the present method, also a machine algorithm can be applied for an automated evaluation.

In an exemplary embodiment, the training of the algorithm was carried out using cells infected with *P. falciparum* in defined cell stages in the setup of Example 1. The malaria-infected cells were selected manually from synchronized cultures of a reference laboratory and spheroidized and detected as in Example 1. A neural network was used for classification of the different malaria stages. One hundred cells for each cell type were used for training. Afterwards, a testing of the neural network was carried out using 200 randomly chosen cells. For obtaining a confusion matrix, all states were considered and evaluated against each other. The results of the training are shown in the following table 1.

TABLE 1

| Confusion matrix from training (I) Confusion matrix (% correct labels) | | | | | |
|---|---|---|---|---|---|
| | Healthy | Ring state | Tropostate | Schizonts | Segmenter |
| Healthy | 98.9 | 1.1 | 0.0 | 0.0 | 0.0 |
| Ring state | 6.7 | 56.0 | 32.0 | 2.7 | 2.7 |
| Tropostate | 2.8 | 16.7 | 75.0 | 5.6 | 0.0 |
| Schizonts | 0.0 | 3.9 | 5.3 | 60.5 | 30.3 |
| Segmenter | 0.0 | 1.8 | 5.3 | 30.9 | 61.8 |

In a further experiment, the same routine of training and testing was carried out as above with regard to the results in Table 1, except that only healthy cells and cells in the ring state were considered. The results are shown in Table 2.

TABLE 2

| | Healthy | Ring state | Tropostate | Schizonts | Segmenter |
|---|---|---|---|---|---|
| Healthy | 98.9 | 1.1 | 0.0 | 0.0 | 0.0 |
| Ring state | 4.8 | 95.2 | 0.0 | 0.0 | 0.0 |
| Tropostate | | | | | |
| Schizonts | | | | | |
| Segmenter | | | | | |

Confusion matrix from training (II)
Confusion matrix (% correct labels)

As can be seen from Table 2, a healthy cell can be discriminated from the ring state with a probability of 95.2%, so that this can form the basis for routine testing for a malaria infection.

By simple fixation and spheroidization of erythrocytes/red blood cells (RBC) alone a malaria infection can already be detected at the earliest ring stage using digital holographic microscopy through a change in optical thickness when a plasmodia is present. In combination with a microfluidic device, a sensitivity comparable to the one achievable in thick film examination can be achieved with a high throughput. Furthermore, the cell cycle of the parasite can be determined by a change in the phase contrast. Digital holographic microscopy furthermore allows determination of the cell volume of an erythrocyte, achieving a further specificity regarding the plasmodia species.

The present method can be easily applied in situations wherein a possible infection of malaria needs to be determined quickly, e.g., at an airport for patients having a fever as, e.g., detected using an infrared camera, etc., in epidemic regions, or in laboratories where a sample of a patient having a possible infection of malaria is tested. A short time for determining the infection form taking a blood sample of the patient to obtaining of results of about half an hour is possible, wherein the measurement itself in the present method can be carried out in as fast as 3 minutes.

The invention claimed is:

1. A method of detecting a possible infection of malaria in a patient, comprising:
providing a digital holographic microscope (DHM),
obtaining or providing a sample comprising at least one red blood cell suspected of being affected by malaria obtained from the patient,
mixing the sample comprising the at least one red blood cell with a buffer solution to form the at least one red blood cell into a sphere shape to form a sphere-shaped red blood cell, and introducing the buffer solution comprising the at least one sphere-shaped red blood cell into a microfluidic device, wherein at least one part of a channel of the microfluidic device is comprised in a focal area of the DHM, or introducing the sample comprising the at least one red blood cell into a microfluidic device, and mixing the sample comprising the at least one red blood cell with a buffer solution to form the at least one red blood cell into a sphere shape to form a sphere-shaped red blood cell, wherein at least one part of a channel of the microfluidic device is comprised in a focal area of the DHM,
guiding the at least one sphere-shaped red blood cell into the focal area of the DHM,
detecting the at least one sphere-shaped red blood cell with the DHM, and
determining whether the at least one red blood cell is affected by malaria to determine whether the patient is infected by malaria.

2. The method of claim 1, wherein the detecting the at least one sphere-shaped red blood cell with the DHM comprises reconstructing the phase and amplitude image obtained by the DHM.

3. The method of claim 1, wherein a cell volume or cell diameter of the at least one sphere-shaped red blood cell is determined with the DHM to identify a development stage and species of a malaria parasite.

4. The method of claim 1, wherein at least ⅔ of a volume of the at least one sphere-shaped red blood cell is detected with the DHM.

5. The method of claim 1, wherein *malaria tertiana*, *malaria tropica*, and *malaria quartana* are differentiated using the DHM.

6. The method of claim 5, wherein a multitude of red blood cells is detected using the DHM, wherein different stages of malaria species are determined for the multitude of red blood cells.

7. The method of claim 6, wherein a parasitemia of the multitude of red blood cells is determined comprising determining the ratio of a number of infected cells to a number of total cells.

8. The method of claim 6, wherein $1*10^4$ to $1*10^6$ red blood cells are detected.

9. The method of claim 1, wherein the at least one red blood cell is isolated from an original sample of the patient, the original sample comprising the at least one red blood cell.

10. The method of claim 9, wherein the original sample of the patient comprises a blood sample.

* * * * *